US00PP34701P3

(12) United States Plant Patent
Olesen et al.

(10) Patent No.: US PP34,701 P3
(45) Date of Patent: Nov. 1, 2022

(54) ***CLEMATIS* PLANT NAMED 'EVIPO104'**

(50) Latin Name: *Clematis viticella*
Varietal Denomination: 'Evipo104'

(71) Applicants: Mogens Nyegaard Olesen, Fredensborg (DK); Raymond J Evison, Guernsey (GB)

(72) Inventors: Mogens Nyegaard Olesen, Fredensborg (DK); Raymond J Evison, Guernsey (GB)

(73) Assignee: Poulsen Roser A/S, Fredensborg (DK)

( * ) Notice: Subject to any disclaimer, the term of this patent is extended or adjusted under 35 U.S.C. 154(b) by 43 days.

(21) Appl. No.: 17/300,629

(22) Filed: Sep. 7, 2021

(65) Prior Publication Data

US 2022/0095515 P1 Mar. 24, 2022

(51) Int. Cl.
*A01H 5/02* (2018.01)
*A01H 6/72* (2018.01)

(52) U.S. Cl.
USPC ..... Plt./228
CPC ..... *A01H 6/72* (2018.05)

(58) Field of Classification Search
USPC ..... Plt./228
See application file for complete search history.

*Primary Examiner* — Susan McCormick Ewoldt

(57) ABSTRACT

A new *Clematis* plant with a compact growth habit, profuse, purple flowers, and continuous summer flowering. The variety successfully propagates from softwood cuttings and is suitable for cultivation in commercial nursery culture. This new and distinct variety has shown to be uniform and stable in the resulting generations from asexual propagation from vegetative cuttings.

2 Drawing Sheets

Botanical classification: Genus: *Clematis*. Species: *viticella*.

Variety denomination: 'Evipo104'.

This application claims priority to Plant Breeder's Rights Application Number 2020/2277, which was filed at the Community Plant Variety Rights Office in the European Union on Sep. 21, 2020, the contents of which are hereby incorporated by reference for all purposes.

SUMMARY OF THE CLAIMED PLANT

The present invention constitutes a new and distinct variety of *Clematis* plant which originated from a controlled crossing between the female seed parent, an un-named seedling, and the male pollen parent, an un-named seedling. Both parent varieties are non-patented.

The two parents were crossed during the summer of 2007 and the resulting seeds were planted the following winter in a controlled environment in Guernsey, Channel Islands, United Kingdom. The new variety named 'Evipo104' originated as a single seedling from the stated cross.

The new *Clematis* plant may be distinguished from its female seed parent and male pollen parent by the following characteristics. The female seed parent grows to a height of 90 cm in one season while the new variety grows to a height of 32 cm in one growing season. The male seed parent has blue tepals while the new variety has purple tepals.

The objective of the hybridization of this *Clematis* plant was to create a new and distinct variety for nursery culture with unique qualities such as:

1. Uniform and abundant purple flowers;
2. Vigorous and compact growth, making the variety suitable for container culture; and
3. Improved disease resistance.

This combination of qualities was lacking in *Clematis* plants that were in commercial cultivation and the qualities have been substantially achieved in the new variety.

'Evipo104' was selected by Mogens N. Olesen and Raymond J. Evison in their *Clematis* development program in the Channel Islands, United Kingdom in 2008. Asexual reproduction of 'Evipo104' by means of vegetative cuttings and traditional layering was first performed by Mogens N. Olesen and Raymond J. Evison in the nursery during the summer of 2008. This initial and subsequent asexual propagations have demonstrated that the characteristics of 'Evipo104' are true to type and are transmitted from one generation to the next.

BRIEF DESCRIPTION OF THE DRAWING

The accompanying color illustrations show as true as is reasonably possible to obtain in color photographs of this type the typical characteristics of the buds, flowers, leaves, and stems, of 'Evipo104'.

Specifically illustrated in FIG. 1 of the drawings are open flowers at various stages of development, tepals detached revealing reproductive flower parts, and flower bud.

DETAILED DESCRIPTION OF THE VARIETY

Figure 1:
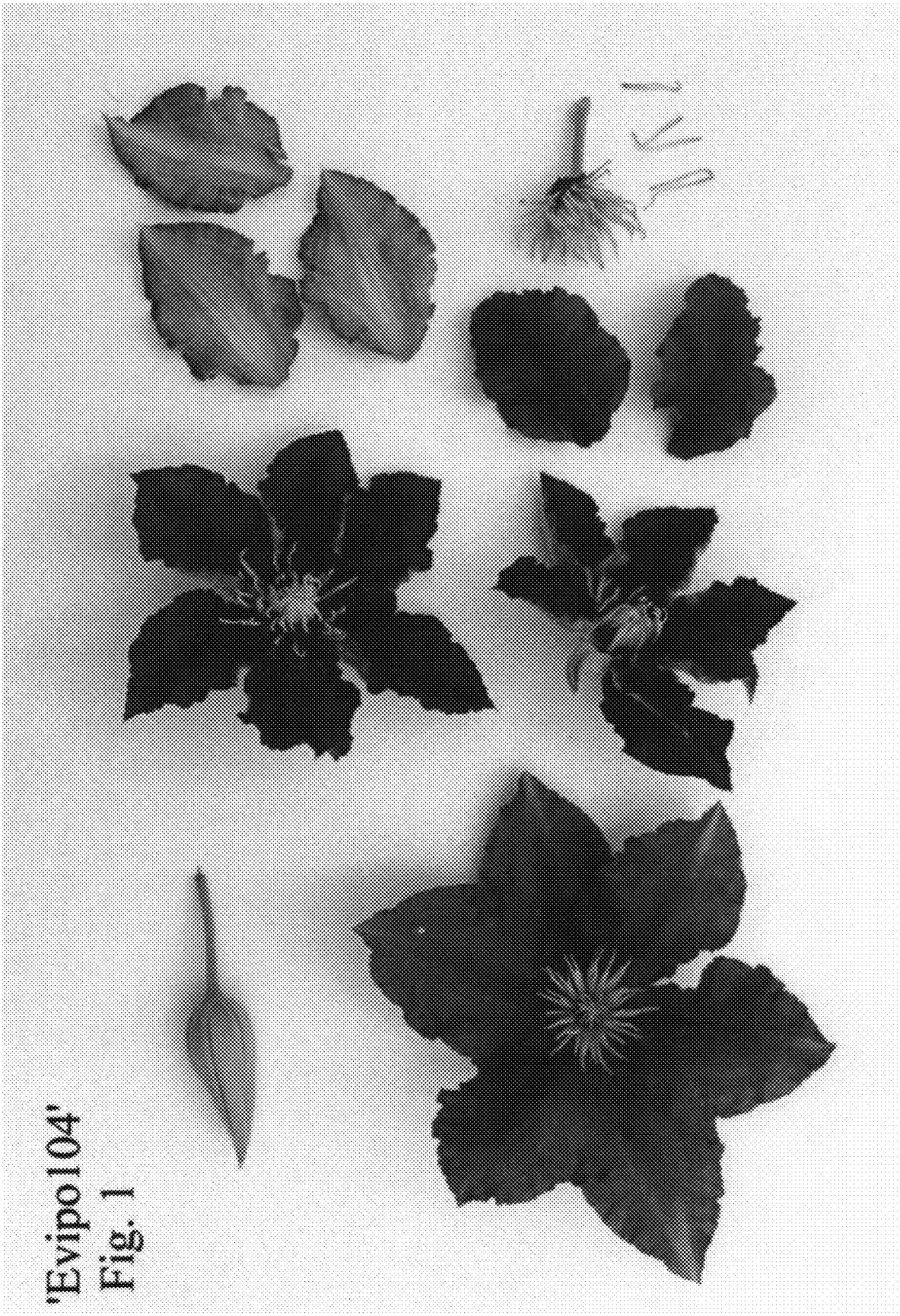
Figure 2:
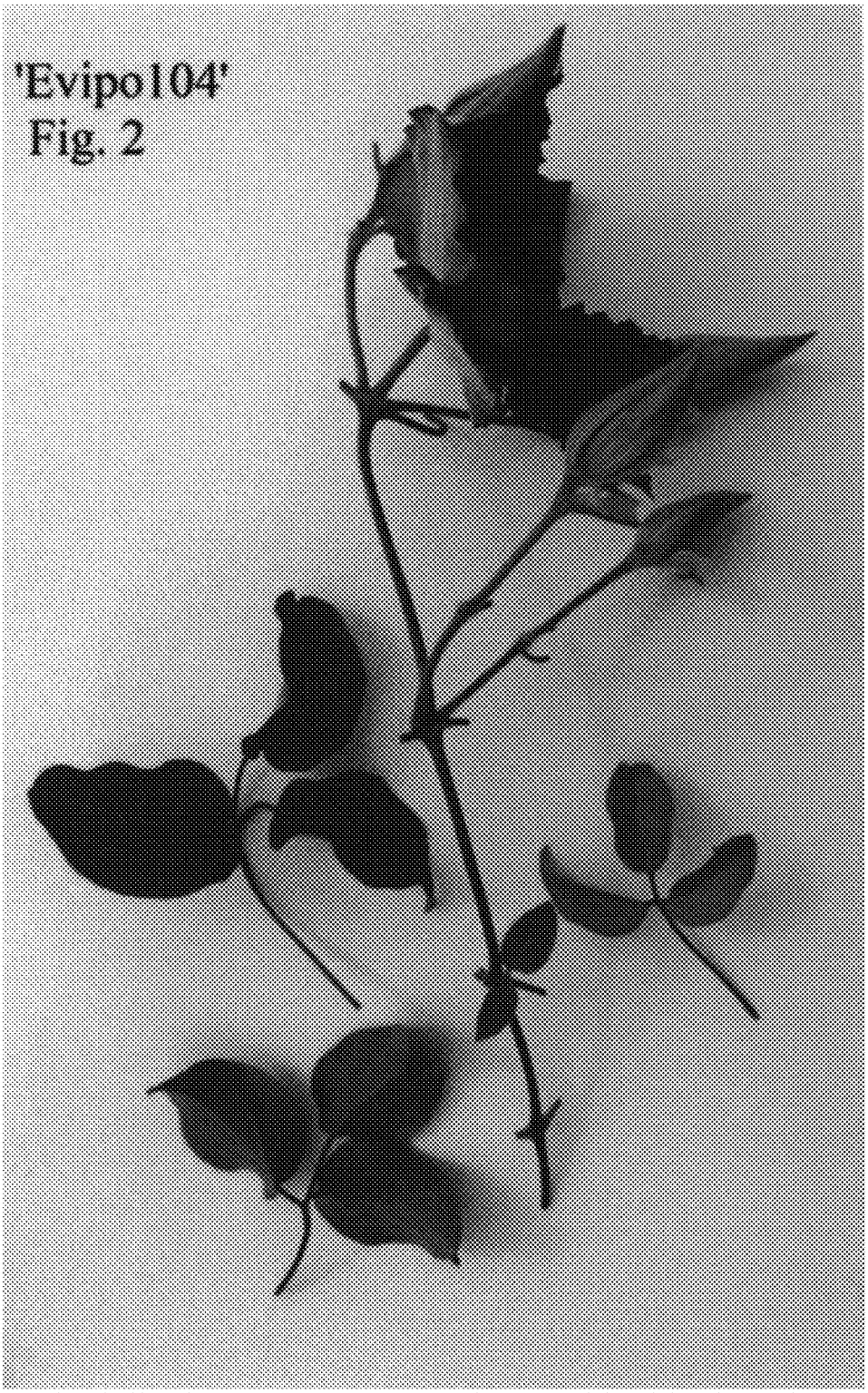
FIG. 2 shows a cluster of flower buds on a branch, leaves detached, and bare stem. Illustrated plants are 2 years of age.

The following is a detailed description of 'Evipo104', as observed in its growth outdoors throughout the flowering period in Odense Denmark. Observed plants were cultivated for a period of 24 months in 2 liter containers. Certain phenotypical characteristics of the variety may vary under different environmental, cultural, agronomic, seasonal, and climatic conditions. Color references are made using The Royal Horticultural Society (London, England) Colour Chart, 2001, except where common terms of color are used.

For a comparison, several physical characteristics of the *Clematis* variety 'Evipo074' described and illustrated in U.S. Plant Pat. No. 28,407 are compared to 'Evipo104' in Chart 1.

CHART 1

| | 'Evipo104' | 'Evipo074' |
|---|---|---|
| Flower diameter | 113 mm | 135 mm |
| Tepal upper surface upon opening | Violet Group N87A blended with Violet Group 83A with a central bar of Violet Group 83D. | Violet Group N88A with a central bar Violet Group N79 B |
| Tepal count | 6 | 6 |

Flower and flower bud:

*Blooming habit.*—Continuous. The natural flowering period is generally from April to September.

*Flower bud.*—Size: Normally 42 mm in length. Bud diameter is 15 mm. Bud form: Long campanulate, broad based. Bud color: Yellow-Green Group 145B. Texture: Very Pubescent.

*Pedicel.*—Surface Texture: Pubescent. Length: On average 22 mm in length with 2 mm diameter. Color: Yellow-Green Group 145A. Strength: Moderately strong.

*Receptacle.*—Surface Texture: Very pubescent. Shape: Broad funnel. Size: 2 mm (h)×4 mm (w). Color: Yellow-Green Group 145A.

*Flower arrangement.*—Location on vine: New growth only. Borne: Singly & in clusters of 3 to 5 flowers.

*Flower bloom.*—Size: On average, flowers are 113 mm in diameter and 25 mm in depth. Profile: Open flowers are flat concave. Fragrance: None. Lasting Quality: Flowers normally remain up to 14 days on the plant.

*Tepals.*—Tepal Color: Upon opening, the upper surface is Violet Group N87A blended with Violet Group 83A with a central bar of Violet Group 83D. The lower surface is Violet Group 86A splashed with w/N155A. There is a central bar on the lower surface of White Group N155A. After opening, the upper surface is Violet Group 86A with a central bar of Violet Group N88A. The lower surface is Violet Group 85B with marginal intonations of Violet 83A, and a central bar of Green-White Group 157A central bar. Quantity: Normally 6 tepals. Size: 56 mm in length by 36 mm wide. Shape: Individual tepal shape is elliptic. The tepal apex is acuminate. The tepal base is obtuse. Apex Recurvature: Strongly curved. Tepal Cross section: Cupped. Margins: Entire with strong undulations. Persistence: Tepals drop off cleanly.

*Reproductive organs.*—Pollen: Quantity: Heavy. Color: Greyed-Yellow Group 160D. Anthers: Size: 6 mm in length. Color: Yellow-Green Group 150B and 150D. Quantity: On average, 35. Filaments: Color: White Group 155A with intonations of Violet-Blue Group 93B at the base. Length: 6 mm. Pistils: Quantity: On average, 25. Stigmas: Inferior in location relative to the length of the filaments and the height of the anthers. Styles: Color: Yellow-Green Group 145B. Length: 13 mm.

*Seed head characteristics.*—Seed not observed to date.

Plant:

*Plant form.*—Mounding.

*Plant growth.*—Very compact.

*Size.*—Seasons growth attains 32 cm in height. Average spread is 35 cm.

*Sterns.*—Color: Juvenile stems are Yellow-Green Group 144B. Mature stems are Greyed-Red Group 179A. Internodes: 40 to 55 mm between nodes. Length: Normally 11 cm from the base of the plant to the flowering portion of the stem. Diameter: About 3 mm. Texture: Mature stems are ribbed. Pubescent.

*Plant foliage.*—Leaf characteristics: Deciduous. Arrangement: Trifoliate. Leaf Size: Compound leaves are about 120 mm (l)×118 mm (w). Leaflets are about 45 mm (l)×31 mm (w). Abundance: On average leaves per 10 cm of stem. Leaf Color: Juvenile upper Yellow-Green Group 144A. Juvenile lower Yellow-Green Group 144A. Mature upper Yellow-Green Group 146B. Mature lower Yellow-Green Group 148C. Stipules: Absent. Petioles: Size: Normally 50 mm in length by 2 mm diameter. Texture: Smooth. Color: Yellow-Green Group 144A. Petioloule: Size: About 11 to 15 mm in length by mm diameter. Texture: Smooth. Color: Yellow-Green Group and Red-Purple Group 183B. Leaflet Shape: Elliptic. The base is rounded, apex acute. Margin: Entire. Surface: The upper side is smooth, the lower side is smooth. Thickness: Moderate. Glossiness: Not glossy.

*Disease resistance.*—Subject to any disease that normally attacks the species. However the variety is more tolerant to *Clematis* wilt, *Ascochyta clematidina*, than some *Clematis* known to the inventors.

*Cold hardiness.*—The variety is tolerant to USDA Hardiness Zone 6.

*Heat tolerance.*—The variety has been found to be suitable for climate conditions found in the American Horticulture Society heat zone 7.

We claim:

1. A new and distinct variety of *Clematis* plant named 'Evipo104', substantially as described and illustrated, due to its abundant purple flowers with good keepability, attractive long lasting foliage and compact growth, year round flowering under glasshouse conditions, suitability for production from softwood cuttings in pots, durable flowers and foliage which make the variety suitable for distribution in the floral industry.

* * * * *

'Evipo104'

'Evipo104'